United States Patent
Cleveland et al.

(10) Patent No.: US 6,645,481 B1
(45) Date of Patent: *Nov. 11, 2003

(54) METHOD OF ACHIEVING OVERNIGHT LAXATION AND CONTROL OF BOWEL FUNCTION

(75) Inventors: Mark vB. Cleveland, Duxbury, MA (US); Russell W. Pelham, Duxbury, MA (US)

(73) Assignee: Braintree Laboratories, Inc., Braintree, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/675,105

(22) Filed: Sep. 28, 2000

(51) Int. Cl.$^7$ ................................................ A61K 31/74
(52) U.S. Cl. ...................... 424/78.01; 424/400; 514/892
(58) Field of Search ............................. 424/78.01, 400; 514/892

(56) References Cited

U.S. PATENT DOCUMENTS

| | | | |
|---|---|---|---|
| 5,710,183 A | | 1/1998 | Halow ......................... 514/723 |
| 6,048,901 A | * | 4/2000 | Cleveland et al. ........... 514/723 |

OTHER PUBLICATIONS

Andorsky et al., Am. J. Gastroent. 85:261(1990).
Attar et al., Gutt 44:226 (1999).
Hammer et al., J Clin. Invest. 84:1056–62(1989).
Hudziak et al., Gastroenterol Clin. Biol. 20:418–23.
Stoltz, R., et al., "An Efficacy and Consumer Preference Study of MiraLax (Polyethylene Glycol 3350) for the Treatment of Constipation in Regular Laxative Users", Home Healthcare Consultant 2001, 8(2) :pp. 21–25.
Chaussade, S. and Minic, M., Comparison of efficacy and safety of two doses of two different polyethylene glycol–based laxatives in the treatment of constipation. Aliment Pharmacol Ther. Jan. 2003; 17 (1) :165–72,pp. 165–175.
Culbert, et al., "Highly Effective Oral Therapy (Polyethyleneglycol/electrolyte solution) for Faecal Impaction and Sever Constipation", Clin Drug Invest.1998, 16 (5) :pp. 355–360.
Di Palma, J.A., et al., "Overnight efficacy of polyethylene glycol laxative", American Journal of Gastroenterology 2002, 97(7) :pp. 1776–1779.

* cited by examiner

Primary Examiner—Thurman K. Page
Assistant Examiner—Charesse Evans
(74) Attorney, Agent, or Firm—Cesari & McKenna, LLP

(57) ABSTRACT

Overnight relief of constipation symptoms is achieved, and control of bowel function is enhanced by oral administration of an effective or sufficient amount of a composition comprising polyethylene glycol (PEG), preferably dispersed and or dissolved in an aqueous medium. The PEG compositions used for the present invention are preferably substantially free of ancillary electrolytes.

29 Claims, No Drawings

METHOD OF ACHIEVING OVERNIGHT LAXATION AND CONTROL OF BOWEL FUNCTION

BACKGROUND OF THE INVENTION

1. Field of the Invention

The present invention relates to the field of laxatives and laxative-based treatments. More particularly, the present invention relates to promoting overnight laxation and control of bowel function in individuals who are otherwise prone to constipation.

2. Background Information

Constipation is a syndrome (a collection of symptoms) that includes the inability to have a bowel movement in a regular fashion, excess flatus or intestinal gas that exists as trapped bubbles that cause feelings of pain, bloating and cramping in the abdominal area. Constipation is the most common gastrointestinal complaint in the United States. Over 4,000,000 people (approximately 2% of the population) have frequent constipation as determined by self-assessment surveys.

Current treatments of constipation fall into two main categories, each with distinct disadvantages. One category, which includes the cathartics or purgatives and the osmotic agents, causes a bowel movement to occur generally within a few hours, in an uncontrollable fashion. That is, a patient who takes a purgative or cathartic laxative has an obligatory bowel movement within minutes to a few hours. The patient is unable to ignore the sensation of urgency, and risks soiling of their garments or gastrointestinal distress from the sense of urgency if they so attempt. The bowel movement due to a cathartic or purgative laxative is characterized by unpredictability and urgency in the patients so that the patients' control of when or where the bowel movement occurs is virtually nonexistent. Examples of these laxatives are bisacodyl, senna, lactulose, saline laxatives and GI lavages.

A second category of laxatives, made up of so-called bulk formers, is composed of digestible or indigestible polymers of carbohydrates and other materials chemically synthesized or appearing in nature, such as psyllium and methylcellulose. While the bulk formers do not produce a sense of uncontrollable urgency, the time course of their efficacy is longer in duration than the cathartics or purgatives. The bulk formers do not produce a bowel movement for as long as two to three days. While the sense of urgency is therefore diminished, the relief is delayed. A more ideal means of treating constipation combines the short time course of efficacy of the purgatives with the lack of uncontrollable urgency that accompanies the bulk formers. Such a product produces overnight relief without urgency, and allows the patient to more readily control the time and place of their bowel movement, providing unique relief to their constipation syndrome.

DESCRIPTION OF THE INVENTION

It has been determined, surprisingly, that a compound—polyethylene glycol, or PEG—known for treatment of constipation has the ideal properties sought. Properly administered, PEG has been found to provide overnight relief of constipation and, at the same time, provides improved control to the patients of the time and place of their bowel movements. A further advantage of the control achieved by use of PEG is that it appears to outlast, for a period of time, the duration of dosing with the compound. In other words, the time period that control is achieved using PEG exceeds the time period for which it is expected that control will be provided. Yet another advantage of PEG is that no increase in dosage amount is required where re-use is needed to obtain the desired treatment results.

This finding is highly unexpected in that the amount of PEG, which produces these effects, is virtually physiologically inert as a cathartic or as bulk former. Although it is considered an osmotic agent, the amount of intestinal water retention that these low doses produce (30 grams) is insufficient to explain the overnight relief. See, for example, Hammer, et al., *J. Clin. Invest.* 84:1056–62 (1989).

Therefore, in accordance with the present invention, overnight relief of constipation and improved patient control of bowel movement timing and place are achieved by oral administration of an effective or sufficient amount of a composition comprising PEG. Preferably, the PEG compositions of the present invention are substantially free of ancillary electrolytes; by "substantially free" is meant containing less than 1% by weight, and desirably as close to 0% as practicable. Alternatively, the PEG compositions may contain ancillary electrolytes. The PEG compositions of the present invention are preferably salt-free, as salts may cross the intestinal mucosa and, due to solvent drag, withdraw water from the intestinal contents, which can increase or induce constipation.

Any food- or pharmaceutical-grade PEG polymer may be employed in the compositions contemplated herein. Polymers of relatively high molecular weight (e.g., above about 900) that are solid at room temperature (i.e., about 25 degree C.) and soluble in (or miscible with) water at room temperature are currently preferred. Polymers having an average molecular weight of at least 1000 (and generally no greater than 20,000) are exemplary, while an average molecular weight between about 3000 and 8000 is preferred; and PEG 3350 (the numeric designation identifying the average molecular weight) is especially preferred.

Compositions according to the present invention are prepared by dispersing and/or dissolving the PEG in water or other aqueous medium to formulate a relatively smooth, palatable drink. PEG is an osmotically active agent that is not significantly absorbed in the abdomen, and may therefore be taken in dosages ranging from about 5 to about 200 g up to four times per day. Preferably, anywhere from 10 to 30 g (depending on symptom severity) of PEG in solid form are conveniently dispersed/dissolved in from about 6 to about 10 fl. oz. (i.e., about 10–12 times the weight of the solid PEG) of water, and the mixture ingested orally up to four times per day as necessary for relief of symptoms. PEG may be furnished in solid form for dispersal in a suitable liquid (e.g., water or juice), or in pre-mixed liquid form, or in solid form for oral ingestion (e.g., as solid wafers, capsules, or tablets).

As shown in Table 1, the efficacy of the invention is demonstrated by clinical trials directed primarily toward measuring the effectiveness and safety as laxatives of the PEG compositions described herein. In a representative study (Braintree protocol 851–3), patients with documented constipation were evaluated for one week (the "control period"). If their bowel habits met the criteria for constipation, they were enrolled into the study and treated with 17 g of PEG 3350 for 14 days (the "treatment period"). There were 48 patients who entered the control phase of this study. During this study, the patients maintained diaries of their bowel habits and of all symptoms experienced during both the control period and the treatment period. The following table shows that the percent of patients who had bowel movements within 24 hours after a single dose of 17 g of PEG increased by 55% over a similar duration during the control period.

TABLE 1

| | 24 Hour Period after Control | 24 Hour Period after 17 g PEG | % Increase over Control |
|---|---|---|---|
| % Patients with BM | 31% | 48% | 55% |

In a second study, as illustrated in Table 2, PEG also increases a patient's sense of control of their bowel movements. "Control" is defined herein as the ability of a patient, upon the feeling of colonic fullness, to have a bowel movement at a convenient time and place, that is without a sense of extreme urgency as seen with cathartic or purgative laxatives. Patients were asked to rate, on a scale of 0 to 100, the ability of a daily 17-gram dose of PEG to produce a sense of "control" of their bowel movements. For control, 0 is equivalent to no control and 100 is equivalent to good control. The study included 72 patients. All of the patients experienced constipation and were occasional laxative users. They were asked to rate the dose of PEG against their usual laxative for its ability to produce control.

The "chi square" statistical procedure was used to determine whether these differences were statistically significant. A "p" value of less than 0.05 is generally accepted as indicating that an observed difference is statistically significant—i.e., that it did not occur by chance. As shown in the data, most patients surveyed reported experiencing greater control following use of the Taxation inducing composition of the present invention (56 subjects, 76%) than those who used the usual laxative (16 subjects, 22%), providing statistical significance of p<0.001.

TABLE 2

| | Usual Laxative (N patients and %) | 17 g of PEG/day (N patients and %) | "p"-value |
|---|---|---|---|
| Laxative with the Most Control | 16 (22%) | 56 (76%) | p < 0.001 |

As demonstrated in Table 3, when the data are analyzed on the basis of the individual laxatives used by the patients, a clear difference between the present invention and the bulk and stimulant laxatives emerges.

TABLE 3

| Patient's Usual Laxative | Usual Laxative (N patients and %) | 17 g of PEG/day (N patients and %) | "p"-value |
|---|---|---|---|
| Fiber/Bulk Laxative | 9 (29%) | 21 (68%) | p < 0.05 |
| Stimulant Laxative | 5 (13%) | 33 (85%) | p <0.001 |

Thus, 17 g of PEG produced better patient control of bowel movements than by use of either fiber/bulk laxatives, such as psyllium or carboxymethylcelluose, or stimulant laxatives, such as sodium phosphate or bisacodyl.

Clinical experience was obtained to measure the duration of effectiveness and safety of the laxative-inducing composition of the present invention with patients who experienced constipation. In the trials, patients reported that they were able to produce satisfactory bowel movements on a daily basis, after taking the composition for 1–4 days. These movements were had with good "control", i.e., with no sense of emergency. however, surprisingly, when these same patients chose to discontinue use of the composition, many reported that they continued to have regular bowel movements daily or every other day, for several days after the cessation of treatment. Thereafter, if they had several days without a bowel movement, they could take the composition for 1–4 days and expect that they could cease therapy and maintain regularity for several days, up to a week or more. Thus, it is shown that a therapy regimen consisting of a few days of taking the composition of the present invention enables a patient to "retrain" the bowel, for at least for several days, so that continuous daily laxative treatment is unnecessary.

Therefore, a dose regimen of the laxation inducing composition of the present invention, lasting for 1–4 days, followed by a "holiday" during which no laxative is given, has been discovered which produces a desirable effect for patients. Such an effect has not been previously appreciated for PEG laxative. The treatment and "holiday" periods of the regimen may be of an equal or unequal duration, as appropriate. Moreover, the regimen may be repeated, as necessary, without increasing the effective dosage amount. The effectiveness of a consistent dosage of a laxative-inducing composition has not been previously appreciated in the art as, where repeated dosing is necessary, the effectiveness of heretofore known laxatives has been predicated increasing the dosage amounts of the laxatives used.

Although the present invention has been described with reference to specific details, it is not intended that such details should be regarded as limitations upon the scope of the invention, except as and to the extent that they are included in the accompanying claims.

What is claimed is:

1. A method of achieving overnight relief of constipation symptoms in a patient experiencing constipation, the method comprising the step of administering a laxation-inducing composition consisting essentially of polyethylene glycol, in an amount sufficient to induce a controlled bowel movement within 12 to 24 hours.

2. The method of claim 1 wherein the composition is substantially free of electrolytes.

3. The method of claim 1 wherein the polyethylene glycol has an average molecular weight greater than 1000.

4. The method of claim 1 wherein the polyethylene glycol has an average molecular weight ranging from 3000 to 8000.

5. The method of claim 4 wherein the polyethylene glycol is PEG 3350.

6. The method of claim 1 wherein the composition comprises a dosage from about 5 to about 200 g of polyethylene glycol.

7. The method of claim 6 wherein the composition comprises from about 10 to about 34 g of polyethylene glycol per dose.

8. The method of claim 7 wherein the composition comprises 17 g of polyethylene glycol per dose.

9. The method of claim 8 wherein the polyethylene glycol is dispersed in an aqueous medium.

10. The method of claim 8 wherein the polyethylene glycol is in solid form.

11. The method of claim 8 wherein the composition is administered up to four times per day.

12. The method of claim 1 wherein overnight relief of constipation symptoms in a patient experiencing constipation is achieved by alternately administering the laxation inducing composition for a first period of time and discontinuing administration of the compound for a second period of time.

13. The method of claim 12 wherein the first and the second time periods are of equal duration.

14. The method of claim 12 wherein the first and the second time periods are unequal in duration.

15. A method of enhancing a patient's control of bowel function, the method comprising the step of administering a laxation-inducing composition consisting essentially of polyethylene glycol, in an amount sufficient to enhance control of bowel function within 12 to 24 hours.

16. The method of claim 15 wherein the composition is substantially free of electrolytes.

17. The method of claim 15 wherein the polyethylene glycol has an average molecular weight greater than 1000.

18. The method of claim 15 wherein the polyethylene glycol has an average molecular weight ranging from 3000 to 8000.

19. The method of claim 18 wherein the polyethylene glycol is PEG 3350.

20. The method of claim 15 wherein the composition comprises a dosage from about 5 to about 200 g of polyethylene glycol.

21. The method of claim 20 wherein the composition comprises from about 10 to about 34 g of polyethylene glycol per dose.

22. The method of claim 21 wherein the composition comprises 17 g of polyethylene glycol per dose.

23. The method of claim 22 wherein the polyethylene glycol is dispersed in an aqueous medium.

24. The method of claim 22 wherein the polyethylene glycol is in solid form.

25. The method of claim 22 wherein the composition is administered up to four times per day.

26. The method of claim 12 wherein control is achieved for several days even after the composition is discontinued.

27. The method of claim 15 wherein the patient's control of bowel function is enhanced by alternately administering the laxation inducing composition for a first period of time and discontinuing administration of the compound for a second period of time.

28. The method of claim 27 wherein the first and the second time periods are of equal duration.

29. The method of claim 27 wherein the first and the second time periods are unequal in duration.

\* \* \* \* \*